(12) United States Patent
Hunsinger et al.

(10) Patent No.: US 9,675,541 B2
(45) Date of Patent: Jun. 13, 2017

(54) WATER-BASED PIGMENTED PREPARATION

(75) Inventors: Ursula Hunsinger, Nuremberg (DE); Zuhal Menguec, Fuerth (DE); Marcus Schwertfeger, Nuremberg (DE)

(73) Assignee: Schwan-STABILO Cosmetics GmbH & Co. KG, Heroldsberg (DE)

( * ) Notice: Subject to any disclaimer, the term of this patent is extended or adjusted under 35 U.S.C. 154(b) by 0 days.

(21) Appl. No.: 13/812,414

(22) PCT Filed: Jul. 22, 2011

(86) PCT No.: PCT/EP2011/003698
§ 371 (c)(1),
(2), (4) Date: Feb. 27, 2013

(87) PCT Pub. No.: WO2012/013323
PCT Pub. Date: Feb. 2, 2012

(65) Prior Publication Data
US 2013/0149364 A1    Jun. 13, 2013

(30) Foreign Application Priority Data
Jul. 28, 2010  (DE) .................. 20 2010 010 755 U

(51) Int. Cl.
| | | |
|---|---|---|
| *A61K 8/04* | (2006.01) | |
| *A61K 8/67* | (2006.01) | |
| *A61K 8/86* | (2006.01) | |
| *A61Q 1/02* | (2006.01) | |
| *A61Q 1/04* | (2006.01) | |
| *A61Q 1/06* | (2006.01) | |
| *A61Q 1/08* | (2006.01) | |
| *A61Q 1/10* | (2006.01) | |
| *C09D 11/00* | (2014.01) | |
| *A61K 8/81* | (2006.01) | |
| *A61K 8/87* | (2006.01) | |
| *C09D 11/18* | (2006.01) | |
| *A61K 8/85* | (2006.01) | |
| *A61Q 1/00* | (2006.01) | |

(52) U.S. Cl.
CPC .............. *A61K 8/86* (2013.01); *A61K 8/8135* (2013.01); *A61K 8/8147* (2013.01); *A61K 8/8182* (2013.01); *A61K 8/85* (2013.01); *A61K 8/87* (2013.01); *A61Q 1/00* (2013.01); *A61Q 1/04* (2013.01); *A61Q 1/06* (2013.01); *A61Q 1/08* (2013.01); *A61Q 1/10* (2013.01); *C09D 11/18* (2013.01); *A61K 2800/594* (2013.01)

(58) Field of Classification Search
CPC .......... A61K 8/345; A61K 8/86; A61K 8/678; A61K 47/48215; A61K 31/355; A61K 8/8147; A61K 8/8152; A61K 8/8182; A61K 8/87; A61K 2800/594; A61Q 1/02; A61Q 1/10
See application file for complete search history.

(56) References Cited

U.S. PATENT DOCUMENTS

| | | | |
|---|---|---|---|
| 3,489,690 A | 1/1970 | Lachampt et al. | |
| 4,826,691 A | 5/1989 | Prochnow | |
| 5,352,696 A | 10/1994 | Kim | |
| 7,144,919 B1 * | 12/2006 | Kim et al. ..................... | 514/458 |
| 2006/0167117 A1 * | 7/2006 | Leaym et al. ................ | 514/876 |
| 2007/0207942 A1 * | 9/2007 | Creutz et al. ..................... | 512/2 |
| 2008/0254075 A1 | 10/2008 | Lugert et al. | |
| 2008/0292570 A1 * | 11/2008 | Bauer et al. .................... | 424/63 |
| 2010/0119560 A1 * | 5/2010 | Kim et al. .................... | 424/401 |

FOREIGN PATENT DOCUMENTS

| | | |
|---|---|---|
| DE | 1593210 C3 | 7/1970 |
| DE | 19959093 A1 | 5/2001 |
| DE | 69902791 T2 | 8/2003 |
| DE | 202007018702 U1 | 2/2009 |
| EP | 1178044 A1 | 2/2002 |
| EP | 1091951 B1 | 9/2002 |
| JP | 2004292410 A | 10/2004 |
| JP | 2006069965 A | 3/2006 |
| KR | 1020013838 A * | 11/2001 |
| WO | 9962896 A1 | 12/1999 |
| WO | 0220508 A1 | 3/2002 |
| WO | 2006028339 A1 | 3/2006 |

OTHER PUBLICATIONS

Kipris machine translation, KR 2001-0100224, downloaded at http://engportal.kipris.or.kr/engportal/search/total_search.do Dec. 4, 2014.*
Mortensen, Macromolecules, 30: 503-507 (1997).*
FDA.gov, "Is It a Cosmetic, a Drug, or Both?", (2012) (p. 1-8), downloaded from http://www.fda.gov/Cosmetics/GuidanceRegulation/LawsRegulations/ucm074201.htm, Sep. 24, 2015.*
Roempp: Anti-settling agent, 2011, http://www.roempp.com/prod/roempp.php.

* cited by examiner

*Primary Examiner* — Kortney L Klinkel
*Assistant Examiner* — Lisbeth C Robinson
(74) *Attorney, Agent, or Firm* — Bachman & LaPointe, PC

(57) ABSTRACT

A water-based pigmented preparation, its production and use and its application in a capillary storage system.

25 Claims, No Drawings

WATER-BASED PIGMENTED PREPARATION

BACKGROUND OF THE INVENTION

The invention concerns a water-based pigmented preparation, its production and use and its application in capillary storage systems.

Water-based liquid preparations, so-called inks, have been known for many centuries. While at the time of the Egyptians such inks were mixed for example with soot and thickened with gum arabic it was already in the third century AD that the first oak gall ink was produced by boiling oak apples with iron sulphate, and it already left a quite permanent colouring behind on the application area. Developments further followed, such as inks with water-soluble dyestuffs and even pigments. After production thereof those water-based preparations were filled in small flacons and could be removed therefrom for example with a fine brush or a quill and thus served as a writing implement or however, depending on the choice of raw material, as a makeup implement, that is to say as a cosmetic ink, for example for colouring the eyelids, the lips or for artistically decorating other parts of the skin, and thus referred to in modern fashion as a tattoo. What is common to those systems which are still often used nowadays is that they contain the colouring substance in dissolved or dispersed form in a liquid which often includes water as the main constituent. While water-soluble dyestuffs are present dissolved in polar solvents, that is to say also water, and thus form a single-phase system, pigments are generally present in the form of an undissolved component in the water phase and therefore form a suspension. A disadvantage with water-based inks with soluble dyestuffs is that in-depth coverage is generally not possible. After drying out at the application area the dyestuff solution always allows the underlying surface to shimmer therethrough. A covering colour layer generally therefore cannot be achieved. In addition dyestuff systems have a tendency to so-called colour drifts, that is to say the colour changes with the storage time, in particular under the influence of light and temperature. The choice of dyestuff is also markedly reduced in comparison with the available pigments.

To produce intensive, multi-coloured, permanent and covering colour shadings, the use of pigments is absolutely essential. Pigments are almost inert in water, and therefore generally do not react under normal conditions with protic solvents, but after evaporation of the solvent form an intensive colour layer which covers the surface depending on the respective pigment content and which lies on the application surface. A disadvantage with pigment-bearing suspensions is that suspensions generally have a tendency to sedimentation. Consequently, because of the relatively high density, the pigments settle in the storage container in the form of a bottom sediment and in time form a solid pigment cake which is difficult to re-disperse. The ink thus loses its colouring properties as the settled pigments can generally no longer be put back into the surrounding liquid in a residue-free fashion. Even with so-called mixing balls or other re-dispersion aids it is often no longer possible to restore the original homogeneity of the ink. Frequently therefore the viscosity of the liquids is increased with rheology additives, usually xanthan gum, gum arabic, acrylic acid thickeners and others until the liquid has attained a gel-like consistency so that settling or sedimentation of the undissolved substances no longer occurs or occurs only to a slight degree. Because of the high viscosity however not only is it more difficult to get the ink out of the storage container but also application in itself is more difficult for the gelatinous material preferably collects at the tip of the applicator device, in the simplest case a brush or a tapered foam tip, and can therefore be only irregularly distributed. The delivery of colour is non-homogeneous, with coverage in the first part of the stroke being markedly stronger while in the second part of the stroke it loses intensity to a considerable degree. Constant uniform delivery of colour is not possible in that way.

To permanently stabilise the colour at the location of application, film-forming agents, that is to say generally film-forming polymers, are frequently used, which after the volatile substances have dried out, leave behind a permanent coloured film. It is desirable for that film in the best-case scenario to be both water-resistant and also rubbing-resistant. Hitherto however it has not been possible to satisfactorily achieve that in purely water-based inks. Current film-forming polymers such as for example polyvinyl alcohols, polyacrylates or polyvinyl pyrrolidones can admittedly be uniformly incorporated into water-based preparations by virtue of their good water-solubility, but they do not form a water-resistant film. The films formed can be easily dissolved off again by wetting with water. It is thus not possible to achieve sufficient resistance to water and rubbing in respect of the coloured films which are formed. Those polymers which could provide permanent water resistance, namely those which are not soluble in water but are only dispersible therein, are also not sufficiently water-soluble to give a homogeneous mixture with the water-based preparation. Those polymers have a tendency to flocculate out, settle or agglomerate in the form of a non-homogeneous constituent, and that has a detrimental effect on the properties of the preparation. To increase compatibility of the water-dispersible film-forming polymer with a water-based preparation, dispersing aids, that is to say in the simplest case surfactants, are added either to the polymer pre-mixture, the so-called polymer dispersion, or however to the water-based preparation itself. Those dispersing aids are also used to provide for better spreading of the preparation at the location of application. Surfactants however reduce the water resistance of the films which are formed and thus detrimentally affect the water and rubbing resistance of the applied preparation.

A development of applicator devices inter alia for reducing settlement or separation of inks and for simplifying their storage and application are systems with capillary storage means. A capillary storage means is a device which includes a porous fibre-like material which has interconnected cavities which preferably have a through-flow direction, namely in the longitudinal direction of the storage means. Suitable materials are for example specific polyester, polyamide or cellulose acetate fibres which are enclosed by a cylindrical film which serves as a casing and thus as a non-spill protection. That storage means is then saturated with the colouring liquid and stores it in the cavities in the interior thereof. Ink flows out of the storage means by the contact of an end of the storage means with the application area, in which case a supplementary delivery of ink is possibly also provided at the same time from a supply storage means disposed on the opposite side. Because of the very small cavities and ducts for transport of the liquid the known pigment-bearing preparations are hitherto not suitable for such storage means. In conventional water-based preparations or inks, even if the pigments can be set to a sufficiently small particle size, the pigments are not sufficiently permanently stabilised with that small particle size of a few micrometres, but reagglomerate instantaneously, which inevitably leads to blockage of the capillary storage means. Therefore in the writing implement industry and also in cosmetics, capillary storage systems are mainly filled with inks involving soluble dyestuffs, single-phase systems which however present the above-mentioned disadvantages such as lack of colour coverage, colour drifts and also so-called 'staining', permanent penetration into and colouring of the parts of the skin, as frequently occurs precisely in cosmetic preparations.

Therefore the problem of the invention is to provide a water-based pigmented preparation which overcomes the disadvantages in the state of the art. The preparation is to be permanently stable, that is to say it is neither to settle, sediment or separate, but is to be easily re-dispersible, without a noticeable application of force. In addition the preparation is to afford water-resistant and rubbing-resistant films. The preparation is to be capable of use with current capillary storage systems and is such that it can be applied by simple application, and it is to have excellent homogeneous colour delivery and colour adhesion.

A further problem of the invention is to provide a process for the production of the preparation.

SUMMARY OF THE INVENTION

Those problems are solved by a preparation and a process as disclosed hereinbelow and defined in allowed claims.

DETAILED DESCRIPTION

It was now surprisingly found that a water-based pigment-bearing preparation which has at least one pigment, at least one water-dispersible film-forming component and at least one polymer ether component, wherein the polymer ether component is of the following formula:

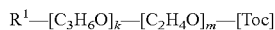

$R^1$—$[C_3H_6O]_k$—$[C_2H_4O]_m$—[Toc]

wherein $R^1$ is any alkyl residue, aromatic residue, acyl residue or H, k is a whole number ≥20, m is a whole number ≥5 and Toc is a tocopheryl residue, overcomes the above-mentioned disadvantages. The preparation according to the invention is settlement-stable even after storage for several months at ambient temperature and even at 45° C., in other words the included pigment or pigments remain homogeneously distributable in the surrounding liquid and therefore do not settle to give a solid pigment cake, but at most form a loose sediment which can be easily homogeneously re-dispersed by simple shaking. The preparation has excellent uniform colour coverage, it can be easily removed from the storage container with conventional applicator means and can be homogeneously applied. A wide colour range of the preparation with the most widely varying colour shades is possible by virtue of the varied pigment availability. Depending on the respective pigment content the coverage capability of the preparation can be individually set. Even inks which are capable of flow, with such a high coverage capability as can otherwise be achieved only with commercially available wax pencil cosmetics, can be achieved by the tremendous stabilisation of the pigments in the water-based preparation. The preparation according to the invention can also be easily applied, that is to say it is workable and has adequate flow capability and wetting capacity. It involves uniform application and permanent adheres at the location of application without migrating or transferring therefrom. In addition the preparation according to the invention is water-resistant, that is to say the colour film which is formed after drying of the preparation, that is to say after evaporation of the volatile constituents of the preparation, does not change visually, even when showered for five minutes with warm water at a temperature of about 35° C., that is to say therefore it neither dissolves away nor varies in colour coverage.

A polymer ether component in accordance with the invention is a chemical compound having at least 20 propylene oxide units, that is to say units of the formula $[C_3H_6O]$, at least 5 ethylene oxide units, that is to say units of the formula $[C_2H_4O]$ or $[CH_2CH_2O]$ and a tocopheryl residue. The propylene oxide (PO) units can be both $[CHCH_3—CH_2—O]$ and also $[CH_2—CHCH_3—O]$ units and the PO segment can contain either only one of the two kinds of propylene oxide units or a mixture of units, wherein the mixture in turn can have statistically distributed PO units and/or blocks of one or both kinds of PO units.

The tocopheryl residue is also bound by way of an ether bond to the polymer ether base body. The further residues $R^1$ can be of any constitution as long as the ether component overall is water-soluble and inert in relation to the pigments used. Thus the residue $R^1$ can be property-neutral or can afford desired properties such as solubility or anchoring. Preferably the residue $R^1$ is H. The residue $R^1$ can however also be a substituted or unsubstituted, linear or cyclic alkyl residue, aromatic residue or acyl residue. The ether component in the case of a cosmetic preparation should also be physiologically acceptable. The polymer ether component thus has a block copolymer structure. It has a polypropylene oxide block and a polyethylene oxide block, wherein the tocopheryl residue is arranged on the polyethylene oxide block at the end.

The expression 'pigment' as is used for the present invention includes inorganic or organic, coloured or non-coloured colouring agents or dyeing agents which are practically insoluble in the medium of use. The term pigments also includes for example lacquers, which are insoluble in water and/or in lipid phases, of organic dyestuffs, glitter agents, pearl sheen agents and other effect agents which are generally known and which are used in writing implements and/or cosmetic products, which also includes polymer particles and silica particles in spherical or flake form.

The term glitter agents or effect agents is used to denote in particular substances based on coated mica, synthetic fluorophlogopite, bismuth oxychloride, coated bismuth oxychloride, glass, metal powder in flake form at least partially coated with other materials, finely divided plastic flakes at least partially coated with other materials, preferably PET flakes or solid solutions of dyestuffs in suitable plastic matrices, preferably in polyester-3.

Quite generally therefore the term pigments is used to denote white or coloured, inorganic or organic particles which in particular are insoluble in water or the medium of application and which are intended to colour and/or cloud the composition. That can involve white or coloured, inorganic and/or organic pigments. For the composition according to the invention the pigments are used in finely ground form, that is to say in a particle size which can move through the capillary openings of capillary storage means. Usually these are particle sizes of below 1 mm, in particular less than 0.2 μm. Pigments with a particle size in the nanometer range, so-called nanopigments, can also be used. Usually the pigments are used in a commercially available size of less than 200 μm, for example about 0.1 to about 200 μm, or with particle sizes in the nanometer range, for example about 5 to about 100 nm, so-called 'nanopigments'. In particular aluminium oxide, titanium dioxide, zinc oxide and cerium oxide are to be named as nanopigments.

The selection of the colouring agents is preferably so effected that their use and the amount used comply with the EU requirements for cosmetics, but also the specifications of Appendix 3 of the Cosmetic Directive for Germany. Comparative regulations are also to be found in Japan and the USA; suitable colouring agents should therefore preferably be so selected that preferably they correspond to the respectively applicable regulations on a world-wide basis.

Of the colouring agents suitable for the composition according to the invention, pigments that are to be mentioned by way of example are titanium dioxide (C.I.-No 77891), iron oxides (C.I. No 77491, 77492, 77499), ultramarine (C.I. No 77007), Berlin Blue/Ferric Blue (C.I. No 77510), soot (carbon black) (C.I. No 77267), chromium oxide green (C.I. No 77288), chromium oxide hydrate green (C.I. No 77289), manganese violet (C.I. No 77742), zinc oxide (C.I., No 77947), barium sulphate (C.I. No 77120), glitter agents such as for example mica, at least partially coated with titanium dioxide (C.I. No 77891), and/or with other metal oxides such as iron oxides, chromium oxide green or chromium oxide hydrate green or with ultramarine and the like colouring agents, bismuth oxychloride and its mixtures with mica (C.I. No 77163), at least partially coated with titanium dioxide and/or others of the aforementioned metal oxides or other colouring agents, flake-form, possibly finely divided metal powders like for example aluminium (C.I. No 77000), copper (C.I. No 77400), bronze (C.I. No 77400), brass (C.I. No 77400), silver (C.I. No 77820) or gold (C.I. No 77480). Organic colouring agents are advantageously selected from the complex salts of carminic acid (C.I. No 75470) and/or colouring agents which were selected from fluoresceins, monoazo dyes, bisazo dyes, indigotin dyes, pyrazol dyes, quinoline dyes, triphenylmethane dyes, anthraquinone dyes, and xanthan dyes which were rendered suitably insoluble by lacquering. The following are to be mentioned here by way of example: FD&C Red No 3 (C.I.-No 45430), D&C Red No 6 (C.I.-No 15850), D&C Red No 7 (C.I.-No 15850:1), D&C Red No 21 (C.I.-No 45380:2), D&C Red No 22 (C.I.-No 45380), D&C Red 27 (C.I.-No 45410:1), D&C Red 28 (C.I.-No 45410), D&C Red 30 (C.I.-No 73630), D&C Red No 33 (C.I.-No 17200), D&C Red No 34 (C.I.-No 15880:1), FD&C Yellow No 5, (C.I.-No 19140), FD&C No 7 (C.I.-No 45350:1), D&C Yellow No 10 (C.I.-No 47005), D&C Orange No 5 (C.I.-No 45370:1), D&C Orange No 10 (C.I.-No 45425:1), FD&C Green No 3 (C.I.-No 42053), D&C Green No 5 (C.I.-No 61570), D&C Green No 6 (C.I.-No 61565), FD&C Blue No1 (C.I.-No 42090), D&C Violet No 2 (C.I.-No 60725). In addition boron nitride as well as silica particles and polymer particles of flake form and also spherical can be used as pigments, which in turn can be mixed or coated with the aforementioned pigments and which are known to the man skilled in the art for example by the term 'light diffusing pigments' (LDP). Particularly preferred pigments are selected from iron oxides, titanium dioxide, zinc oxide, carbon black, carmine, ferric ferrocyanide, chromium hydroxide green, chromium oxide green, manganese violet, ultramarine blue and Yellow 5 as they allow particularly good colour coverage and the production of most mixed colours.

Without being bound down to a theory it is assumed that the combination according to the invention of PO units, EO units and tocopheryl residue which form the polymer ether component on the one hand stearically prevents the pigment particles from sedimenting or caking together while on the other hand it leads to a very stable long-lasting application. It is assumed that the three constituents co-operate in the optimum fashion, wherein the PO block encases the pigment particles so that agglomeration and the sedimenting tendency of the pigments is markedly reduced. It is further assumed that the water solubility of the block of ethylene oxide units in the ether component leads to more uniform distribution in the water phase. Finally it is assumed that the terminal tocopheryl residue contributes to further stabilisation and anchoring of the particles.

The block of ethylene oxide units provides as part of the ether component according to the invention, by virtue of its water solubility, that the particles remain distributed in the aqueous medium. By virtue of the structure of the ether component the EO units project virtually radially or outwardly from the pigment particles encased or enclosed by polypropylene oxide units and can thus contribute to keeping the individual pigment particles at a spacing from each other. In that way the pigment particles can be distributed uniformly in the dispersing agent or solvent surrounding them without the pigment particles encased by the polypropylene oxide units agglomerating and sedimenting. In other words it is to be assumed that the finely distributed pigment particles of the ether component according to the invention, or the PO block thereof, are encased by virtue of the affinity of the polypropylene oxide units to those pigments and that the encased pigments are held in suspension in the aqueous medium by the outwardly directed water-soluble ethylene oxide units. That kind of stearic shielding effectively prevents agglomeration and settlement of the pigments, the pigments are kept in suspension and are thus prevented from sedimenting or at least agglomerating. If pigment particles settle they at most form a loose sediment which can be easily re-dispersed. The problem that individual pigment particles come into direct contact with each other and form a solid pigment segment is thus surprisingly prevented by use of the ether component according to the invention.

It was found that to achieve adequate stabilisation of the preparation the units having a stabilising action must be present in an adequate amount. It was found that the ether component must have at least 20 PO units for protective encasing of the pigment particles. With a smaller number of PO units encasing of the pigment particles is no longer reliably ensured so that particles can agglomerate. The higher the proportion of propylene oxide units, the denser is the casing around the pigments and pigments and thus the entire preparation can thus be better stabilised. Good results are achieved if the polymer ether component has at least 40, preferably at least 50 and particularly preferably at least 60 propylene oxide units. Limits are imposed upwardly here only insofar as the ether component should be homogeneously soluble in the water phase without forming a double phase, which can become difficult with an excessively high number of PO units.

In addition a minimum number of 5 EO units is necessary to achieve adequate water solubility. With fewer than 5 EO units the water binding capacity is insufficient to hold the pigment particles stable in the aqueous phase. A minimum number of 5 ethylene oxide units is necessary for adequate water dispersibility of the pigment particles, for stabilisation and to permanently prevent settlement of the pigments. The higher the proportion of ethylene oxide units, the correspondingly better is the water dispersibility of the pigment ether component unit. Good results are achieved if the ether component according to the invention contains at least 50, preferably at least 80 and particularly preferably at least 100 or more, for example 200, ethylene oxide units.

It has been found that an ether component which has at least 20 propylene oxide units (in the foregoing formula $k \geq 20$) and at least 5 ethylene oxide units (in the foregoing formula $m \geq 5$) per molecule guarantees adequate stabilisation of the pigments in the preparation as then the proportion of propylene oxide units with high affinity for the pigments and the number of water-soluble ethylene oxide units is sufficiently high so that a stable stearic shielding protective casing is formed around the pigment particles, and that permanently counteracts settlement of the pigments and also the formation of a solid pigment cake in the preparation.

The third essential constituent of the ether component according to the invention is a tocopheryl residue. The tocopheryl residue is bound to the EO block at the end by way of an ether bond. It was surprisingly found that the presence of a tocopheryl residue, possibly because of its lipophilia, contributes to stabilisation and also markedly increases the durability of a film formed from the preparation according to the invention. Possibly the tocopheryl residue acts as an anchor between the ether component and the applied surface on the one hand and the film-forming component and the ether component on the other hand, whereby the pigment particles are anchored or both linked together in or at the film-forming component so that the result is a particularly durable uniform film on the applied surface, which does not migrate away and which is not transferred.

Without being bound down to a theory it is further assumed that the tocopheryl residue contributes to stabilisation by virtue of its lipophilia, insofar as it stabilises lipophilic components in the water-based preparation. In the ether component according to the invention the tocopheryl residue is bound at the end to the block formed by the ethylene oxide units and thus projects into the aqueous phase from the pigment particle surrounded by propylene oxide units. While the ethylene oxide units forming the EO block carry water molecules which prevent consolidation of the ethylene oxide blocks the lipophilic tocopheryl residues project into the surrounding water phase. Lipophilic components which can otherwise be stabilised exclusively by dispersing aids in the water phase can now interact with the lipophilic tocopheryl residues and be carried thereon. By virtue of the homogeneous distribution of the tocopheryl residues bound to the ether component according to the invention which encloses the pigment particles lipophilic components of the preparation can be permanently uniformly kept distributed in the preparation by interaction with those lipophilic tocopheryl residues, thereby further promoting the stability of the overall preparation. For example a film-forming component having a lipophilic region can be added to the tocopheryl residue. When a tocopheryl residue of an ether component encasing another pigment particle is also added at the other side of the film-forming component then the film-forming component can function as a bridge or spacer between the tocopheryl residues and thus between the encased pigment particles.

By virtue of the lipophilic interactions between tocopheryl residue/film-forming component/tocopheryl residue therefore the tocopheryl residue can also contribute to the water-dispersible film-forming component according to the invention being uniformly distributed in water and stabilised, while at the same time also effectively preventing or at least markedly reducing agglomeration or settlement of the pigment particles.

If nonetheless settlement of the pigment particles in the preparation occurs after prolonged storage the composition according to the invention prevents the particles from agglomerating. Instead only a loose composite which can be easily re-dispersed by simple shaking is formed.

At the same time the above-described arrangement of the components according to the invention, after application of the preparation, can act like an 'anchoring' of pigment particles in the film formed and thus retain the pigment particles in or on the film in such a way that bleeding-out, running or transfer can no longer occur.

When more specifically the preparation according to the invention is applied to the place of application the solvent water and possibly other volatile components including the water which is 'incorporated' between the ethylene oxide units evaporates. The lipophilic components, that is to say in particular the film-forming component, remains however anchored to the tocopheryl residues and is thus stabilised at the place of application. Accordingly the pigments encased by the ether component are also permanently bound to the place of application. That leads to outstanding film formation and the production of a homogeneous colour layer which does not migrate or suffer transfer.

To achieve the advantageous properties of the preparation according to the invention therefore all three constituents—PO block, EO block and terminal tocopheryl residue—are required.

The amount of ether component according to the invention should be in a range of 1 to 30% by weight to apply the advantageous properties of the preparation. The respectively optimum amount which can be easily determined by the man skilled in the art depends inter alia on the nature of the respective compound used, for example the proportion of PO and EO units respectively, and also on the nature and amount of the pigments used as well as the further constituents in the preparation. Good results are achieved in a range of 1.5 to 10% by weight and preferably 2 to 5% by weight with respect to the total weight of the preparation. Amounts of less than 1% by weight with respect to the total weight of the preparation do not have a sufficiently stabilising influence on the preparation according to the invention. Amounts of more than 30% by weight with respect to the total weight of the preparation in contrast do not lead to a considerable further increase in the settlement stability of the preparation and are therefore uneconomical. The increase in stabilisation due to the ether component no longer increases linearly with the amount in a range of 5 to 10 and further up to 30% by weight. The optimum amount, that is to say the maximum stabilisation effect, with the lowest possible concentration, is therefore in a range of about 2 to 5% by weight with respect to the total weight of the preparation. With an optimum concentration of polymer ether component even high pigment contents of up to 20% by weight can be adequately stabilised. The man skilled in the art can easily ascertain that optimum concentration by routine experiments.

As described above, besides a tocopheryl residue, the ether component according to the invention has both ethylene oxide units and also propylene oxide units. The ratio of propylene oxide units to ethylene oxide units in those block polymers is not critical per se as long as there are sufficient PO units for encasing the pigment particles and sufficient EO units for water dispersibility of the encased particles. A ratio of propylene oxide units to ethylene oxide units in the range of 10:1 to 1:10 has proven to be suitable, it is preferably between 5:1 and 1:10, more preferably between 5:1 and 1:5. It was found that a higher proportion of ethylene oxide units than propylene oxide units imparts rather more stability. The higher the proportion of ethylene oxide units in comparison with propylene oxide units, the correspondingly greater is the water solubility of the ether component and thus the distributability and re-dispersibility of the pigments encased by the ether component. Particularly preferred ether components are known by their INCI (International Nomenclature of Cosmetic Ingredients): PPG-20 Tocophereth-5, PPG-20 Tocophereth-50, PPG-30 Tocophereth 70 and PPG-70/

Tocophereth-100, in particular PPG-70/Tocophereth-100. They lead to particularly good stabilisation of the pigments in the surrounding water phase.

As already mentioned, as a further component which is essential to the invention, the preparation according to the invention includes a water-dispersible, non-water-soluble film-forming component. Film-forming components in accordance with the invention are compounds which are present in an aqueous phase in finely divided distributed form but not dissolved. They can be aqueous polymer emulsions or suspensions, that is to say the film-forming compound can be distributed or can be distributable in the form of small droplets or small particles in the water phase. Both aqueous dispersions and dispersible polymer powders can be used for production of the preparation according to the invention, preferably aqueous dispersions are employed. In this case such a film-forming compound which is/can be dispersely distributed in the finished preparation in the aqueous phase without being dissolved must be used. Preferably lipophilic or lipophilicly-modified film-forming polymers are used.

In addition such a compound or mixture of compounds which after drying of the preparation leaves a permanent film behind at the place of application is used as the film-forming component. The film formed from the preparation according to the invention can act like a protective film for the pigments and other components of the preparation according to the invention and stabilise same at the place of application, and it prevents components being transferred or migrating from the application area. Suitable film-forming components which are not water-soluble but water-dispersible are sufficiently known both from the writing implement industry and also from cosmetics and the generally known film-forming agents can also be used for the purposes of the present invention. For example polyacrylates, polyurethanes, polyvinyl acetates, polyesters and derivatives thereof as well as copolymers and block copolymers thereof are suitable. It is also possible to use mixtures of said polymers, copolymers and/or block copolymers. Preferred film-forming components contain polyacrylates and/or polyurethanes and their mixtures and copolymers. Styrene/acrylates/ammonium methacrylate copolymer, polyurethane copolymers and acrylate/octylacrylamide copolymers have proven to be particularly suitable as they also increase the water resistance of the film which is formed and are highly compatible with the components which are essential to the invention.

The water-dispersible film-forming components according to the invention can be distinguished from water-soluble film-forming components which are not suitable according to the invention, in that they do not form clear solutions. When a film-forming component according to the invention is mixed with water in the application concentration, a cloudy composition is produced. They generally form finely distributed droplets or particles in water, which are distinguished by a cloudy appearance even with low levels of concentration of 10% by weight in water. In contrast thereto water-soluble film-forming agents in the concentration of use in water form a clear composition. Water-soluble or colloidally soluble film-forming components form clear, that is to say transparent mixtures, with water.

Aqueous polymer dispersions used according to the invention generally contain the polymer in the form of finely divided particles or droplets with a particle size/droplet size in the range of about 0.1 to 5 µm. Dispersions with particles of a size of less than 20 nm are colloidally dispersible and are not used according to the invention.

Another advantage of the preparation according to the invention is that, by virtue of the stabilising action of the ether component, surfactants, which as mentioned in the opening part of this specification, are usually required for uniform distribution of film-forming components in the aqueous phase can be omitted or used in a reduced amount. That is advantageous in particular because surfactants can adversely affect the film-forming properties and the water resistance of the films formed.

It has surprisingly been found that the ether component according to the invention serves not only as a pigment stabiliser but also as a dispersing aid for the film-forming component according to the invention without in that respect adversely affecting the film-forming properties thereof. Thus, by using the ether component according to the invention in combination with a film-forming agent which is essential to the invention, it is possible to impart water resistance and rubbing resistance to the preparation. That seems to be attributed to the fact that, as already stated, the lipophilic tocopheryl residue interacts particularly well with the lipophilic or lipophilicly modified film-forming polymer and anchors the film-forming component to the tocopheryl residue. The lipophilic tocopheryl residue at the otherwise water-soluble ether component thus serves as a binding member between the lipophilic film-forming component and the hydrophilic solvent phase.

Therefore only a combination according to the invention of ether component and film-forming component leads to a preparation which is distinguished by outstanding homogeneity, excellent water resistance, rubbing resistance, uniform delivery of colour and permanent colour intensity and can form permanent colour-intensive films.

To permit adequate film formation of the preparation according to the invention the film-forming component should be contained in an amount of 0.25 to 10% by weight, wherein the concentration detail relates to the amount of polymer with respect to the overall preparation. The amount depends on the nature of the polymer or polymers used and the respectively optimum amount can easily be determined by the man skilled in the art in routine tests. Good results are achieved with a proportion of 2 to 20% by weight, particularly preferably 4 to 10% by weight, with respect to the total weight of the preparation. An amount of less 1% is weight is generally not sufficient to form a uniform permanent film. If the amount of film-forming agent in the preparation is over 30% by weight then dispersibility and fluidity are generally no longer sufficient.

The water-dispersible film-forming component according to the invention can be added as a pure substance or as a previously formed aqueous dispersion. Previously produced aqueous mixtures are commercially available or can be produced from pure substances, in generally they contain the film-forming agent in an amount of about 30 to 40% (% by weight) of film-forming component in the aqueous mixture.

A further essential constituent of the preparation according to the invention is the pigment, as described above. The pigment content of the preparation according to the invention can be selected as desired according to the respective colouring properties of the selected pigment and according to the desired colour intensity. Contents of a few percent by weight, for example 1% by weight or more, with respect to the total weight of the preparation, are often sufficient for light colour shades. For stronger colours as are necessary in particular for writing implements or eyeliner the pigment content can be up to 20% by weight with respect to the total weight of the preparation. Quantitative proportions of over 20% by weight are possible in individual cases, but can increase the viscosity of the preparation to such an extent that the fluidity is no longer sufficient to transport the preparation through the capillaries. Preferably therefore the content of pigment is 5 to 15% by weight and particularly preferably 7 to 12% by weight with respect to the total weight of the preparation. With 7 to 12% by weight of pigment the preparations obtained have good coverage and are colour-intensive, as are desirable both in the writing implement industry and also in cosmetics.

As the preparation according to the invention can be intended for use in capillary storage implements, the particle size must be suitably adapted so that the particles can slide through the capillaries. The particle size also has an influence on the colouring properties of the pigments. The smaller the pigment particles which are used in the preparation according to the invention are, the correspondingly more colour intensive and of a colour of greater uniformity is the preparation.

Therefore pigment particles of a particle size of less than 15 µm are desirable. Due to the incredible stabilisation of the pigments by their being enclosed with the ether component according to the invention, it is possible to permanently stabilise even very fine pigment particles without their agglomerating even upon storage at ambient temperature or 45° C. over several months and producing pigment agglomerates of substantially larger diameter than originally present. Rather, even very fine pigment particles are so well protected by the ether component according to the invention that even adjacent pigment particles remain spatially separated from each other and the risk of the formation of pigment cakes and pigment aggregates is markedly reduced. The particle size in the preparation according to the invention is therefore generally less than 15 µm, preferably less than 10 µm and particularly preferably less than 5 µm. The combination according to the invention of pigment and propylene oxide-bearing ether component means that even pigment particles of less than 1 µm can be permanently stabilised. In that respect the desired pigments are already used in the form of micronised pigments of the desired particle diameter or alternatively larger pigment agglomerates are set to the desired particle diameter in situ by suitable comminution measures, for example by means of a ball mill or a homogeniser. The polymer ether component then encases the pigments dispersed in the water phase and stabilises the pigment particles.

It should also be mentioned that the pigment particles, when encased by the ether component according to the invention and dispersed in the aqueous phase, appear to have a larger particle size as the EO block absorbs water. That however does not have any detrimental effects on the fluidity in the capillary as the movement of the particles therethrough is determined only by the size of the solid pigment particles while the more voluminous water casing can be suitably deformed when passing through the capillaries so that the particles do not remain caught up.

The preparation according to the invention can contain further ingredients as are usual for such products such as humectants, preserving agents, perfumes and so forth and may also include one or more surfactants.

Preferably the preparation according to the invention contains at least one humectant. Suitable humectants are monovalent and polyvalent alcohols, urea derivatives and vegetable extracts, in which respect propylene glycol, methyl propane diol and butylene glycol are particularly preferred as they are excellently well incorporated into the preparation according to the invention without destabilising it. Surfactants which can be used for the preparation according to the invention but which do not have to be are employed to reduce the surface tension of the water phase and to achieve better spreading on the application area. The man skilled in the art selects suitable surfactants from the commercially available surfactants. The man skilled in the art can also easily ascertain the amounts of commercially available raw materials by routine experiments.

The preserving agents and perfumes which are usual for writing or cosmetic pencils are suitable as the preserving agents and perfumes and, if present, are used in the usual amounts.

The preparation according to the invention is distinguished by extraordinarily high stability. The pigments dispersed therein are stabilised so well that irreversible sedimentation is prevented. At most a loose pigment bed which can be re-dispersed again without major complication and expenditure is formed due to encasement of the pigment particles with the polymer ether component according to the invention.

That tremendous stabilisation of the very fine pigment particles provides water-bearing colouring preparations which have a high covering capability and colour intensity as well as colour depth. Because the pigments are stearically prevented from forming agglomerates or forming a solid sediment cake the preparation according to the invention is suitable in particularly also for capillary storage systems, as were described in the opening part of this specification. By virtue of the fine pigment particles being permanently encased and by virtue of stabilisation thereof, blockage of the capillary passages and pores is prevented. If hitherto the use of pigments in capillary storage means was not possible by virtue of the tendency of the pigments to agglomerate, the preparation according to the invention now permits precisely that application. That is especially the case as it is possible to dispense with conventional rheology additives. Such viscosity-regulating additives admittedly improve the stability of the preparation but they reduce the fluidity of the preparation to such a great degree that the preparation can no longer be used for capillary storage systems. The preparation according to the invention however provides that it can still flow through the capillary storage means, even after months-long storage at 45° C. and storage in various positions. Settlement of the pigments or agglomerations does not occur in the capillaries of the capillary storage system.

The preparation according to the invention is suitable both as an ink for writing implements and also—in accordance with the respective choice of the components—for cosmetics, for example as blusher, eyeliner, lip ink, lipliner, eyeshadow, mascara or eyebrow ink. The subject-matter of the invention is therefore also a pencil which includes a capillary storage means and a preparation, as described hereinbefore.

In particular the invention provides writing pencils and cosmetic pencils having a capillary storage means filled with the preparation according to the invention. The pencils can be in the form of lipliners, eyeliners or eyebrow pencils, with which very thin lines can be drawn, or however also in the form of pencils with a wider application suitable for applying coloured layers to lips and cheeks. Capillary storage pencils which are suitable for applying thin and wide lines by virtue of the form of applicator can be filled with the preparation according to the invention and are part of the present invention. Upon use, a line is drawn with the pencil at the desired location, for example an eyeliner stroke, or a layer of the coloured preparation is applied, for example to the lips. The result is a uniform long-lasting layer. Even after a prolonged storage time the pencil according to the invention can still be used to draw uniform lines or apply uniformly coloured layers.

The preparation according to the invention can be produced by grinding the pigments and adding the components according to the invention. The subject-matter of the invention is therefore also a process for the production of the preparation according to the invention, comprising the following steps:

a) dispersing at least one pigment in water or in aqueous phase, b) adding at least one polymer ether component of the following formula:

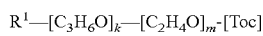

wherein $R^1$ is any alkyl residue, aromatic residue, acyl residue or H, k is a whole number ≥20, m is a whole number ≥5 and Toc is a tocopheryl residue, c) optionally grinding the at least one pigment to the desired particle size, d) adding at least one water-dispersible or water-dispersed film-forming component, and e) homogenising the preparation.

To produce the preparation according to the invention the pigments can be finely ground in water or the aqueous phase which at that time can also already contain the ether component according to the invention, until its particle diameter is in the desired range, for example less than 1 μm. The particle diameter can be determined by laser diffraction. In the present case a Microtrac Blue Wave device was used both for determining the particle size of the polymer components used and also the pigment particles and particles in the preparation according to the invention. If the ether component was not already presented with the water, it can be added following the grinding step or later with the film-forming component. The ether component can be added at any time prior to or during the grinding step or also after grinding. To prevent agglomeration of the pigments they should be added as soon as possible. Preferably they are added prior to or after the grinding step. The film-forming component and optionally other usual components are added with agitation with an impeller agitator. The mass can be stored in a tightly closed storage container.

The preparation according to the invention will now be described by means of the Examples hereinafter which however are in no way intended to be definitive. The raw materials are specified with their INCI, as far as possible. Their quantitative details relate to percent by weight and are related to the total weight of the preparation unless otherwise stated.

EXAMPLES

To determine the viscosity of the preparation a rotational rheometer having a plate-plate measuring system was used, the diameter of the plates being 50 mm in each case and the gap spacing d being 1 mm. Viscosity was measured at 25° C. The shear rate was 100 $s^{-1}$.

The operation of determining the degree of water resistance was carried out as follows: the preparation to be tested was applied in the form of a square of an area of 1 $cm^2$ to the skin, cleaned with cleaning agent and water, at the forearm of a test person, followed by waiting for 15 minutes. The skin area was then rinsed with water at a temperature of 34 to 36° C. at a spacing of 10 cm for 5 minutes. The flow rate of the water was 3.2 l/min in that case. Water resistance was determined visually. The material was identified as being water-resistant if no change was to be seen optically either in colour intensity or in film stability.

Measurement of the particle sizes was ascertained by means of a Microtac Blue Wave device using laser diffraction.

A storage means of a length of 70 mm and a diameter of 7.4 mm was used as the capillary storage means. The capillarity was 3.8 cm and the capacity of the storage means was 1.52 $cm^3$. A polyester fibre served as the fibre material. The wall material was extruded polypropylene. Such a capillary storage means was introduced into a suitable fibre pencil.

Example 1

Water-Based Ink I

| Raw material | Amount in % wt |
|---|---|
| AQUA | ad 100 |
| TITANIUM DIOXIDE 77891 | 2.86 |
| FERRIC FERROCYANIDE 77510 | 2.86 |
| IRON OXIDES 77491/77492/77499 | 2.86 |
| PPG-70 Tocophereth-100 | 4.70 |
| PROPYLENE GLYCOL | 8.20 |
| POTASSIUM SORBATE | 0.50 |
| Phenoxyethanol | 1.00 |
| SORBITAN LAURATE + POLYGLYCERYL-10 LAURATE | 5.50 |
| AQUA + PPG-17/IPDI/DMPA COPOLYMER (70% wt AQUA) | 20.00 |

The water was provided, the pigments were added and ground up with a rotor-stator dispersing tool (Ultra-Turrax) at a maximum rotary speed for 10 minutes. In a separate container propylene glycol and the PPG-70 Tocophereth-100 are melted at 50° C. and that mixture was quickly added with agitation to the pigment dispersion. Then in each case with agitation first the surfactant, thereafter the preserving agents and lastly the polymer dispersion were added. The mixture was agitated for a further 15 minutes and introduced into fibre tip pens and into containers of a 4 ml filling capacity. A peppermint-coloured ink was obtained in that way.

The ink had a viscosity of 14 mPa·s. The particle size (maximum of number distribution) was 0.09 μm.

The material could be removed from the containers with a hair brush and applied well to the skin. Likewise the material could be applied to the skin with the fibre tip pen. The colour delivery was homogeneous and gave good coverage and the surface of the film formed was pleasantly soft. The film did not tighten on the skin and did not crack open even due to movements of the application area.

The dried ink films obtained in that way had a high coverage capability, they were wipe-resistant and water-resistant.

The material formed a sediment which had a relative sediment height of 0.75 in the storage vessels after a storage period of three months at ambient temperature. By simply stirring up the material the sediment was re-dispersed and after the then subsequent application presented properties of unchanged quality: a renewed smear of colour, compared to that from the original, unstored material, was evidently identical, no colour drift was to be observed and the colour intensity was also identical to the unstored material.

Example 2

Water-Based Ink II

| Raw material | Amount in % wt |
|---|---|
| AQUA | ad 100 |
| TITANIUM DIOXIDE 77891 | 5.00 |
| FERRIC FERROCYANIDE 77510 | 5.00 |
| PPG-70 Tocophereth-100 | 4.70 |
| PROPYLENE GLYCOL | 8.20 |
| POTASSIUM SORBATE | 0.50 |
| Phenoxyethanol | 1.00 |
| SORBITAN LAURATE + POLYGLYCERYL-10 LAURATE | 5.50 |
| Ammonium acrylates copolymer + AQUA (70% wt AQUA) | 20.00 |

The water was provided, the pigments were added and ground up with a rotor-stator dispersing tool (Ultra-Turrax) at a maximum rotary speed for 10 minutes. In a separate container propylene glycol and the PPG-70 Tocophereth-100 are melted at 50° C. and that mixture was quickly added with agitation to the pigment dispersion. Then in each case with agitation first the surfactant, thereafter the preserving agents and lastly the polymer dispersion were added. The mixture was agitated for a further 15 minutes and introduced into fibre tip pens and into containers of a 4 ml filling capacity. A light blue ink was obtained in that way.

The ink had a viscosity of 24 mPa·s. The particle size (maximum of number distribution) was 0.09 μm.

The material could be removed from the containers with a hair brush and applied well to the skin. Likewise the material could be applied to the skin with the fibre tip pen. The colour delivery was homogeneous and gave good coverage and the surface of the film formed was pleasantly soft. The film did not tighten on the skin and did not crack open even due to movements of the application area.

The dried ink films obtained in that way had a high coverage capability, they were wipe-resistant and water-resistant.

The material formed a sediment which had a relative sediment height of 0.70 in the storage vessels after a storage period of three months at ambient temperature. By simply stirring up the material the sediment was re-dispersed and after the then subsequent application presented properties of unchanged quality: a renewed smear of colour, compared to that from the original, unstored material, was evidently identical, no colour drift was to be observed and the colour intensity was also identical to the unstored material.

Example 3

Water-Based Ink III

| Raw material | Amount in % wt |
|---|---|
| AQUA | ad 100 |
| TITANIUM DIOXIDE 77891 | 5.00 |
| FERRIC FERROCYANIDE 77510 | 5.00 |
| PPG-70 Tocophereth-100 | 4.70 |
| BUTYLENE GLYCOL | 8.20 |
| POTASSIUM SORBATE | 0.50 |
| Phenoxyethanol | 1.00 |
| SORBITAN LAURATE + POLYGLYCERYL-10 LAURATE | 5.50 |
| Polyurethane-2 and polymethyl methacrylate + AQUA (60% wt AQUA) | 20.00 |

The water was provided, the pigments were added and ground up with a rotor-stator dispersing tool (Ultra-Turrax) at a maximum rotary speed for 10 minutes. In a separate container butylene glycol and PPG-70 Tocophereth-100 are melted at 50° C. and that mixture was quickly added with agitation to the pigment dispersion. Then in each case with agitation first the surfactant, thereafter the preserving agents and lastly the polymer dispersion were added. The mixture was agitated for a further 15 minutes and introduced into fibre tip pens and into containers of a 4 ml filling capacity. A light blue ink was obtained in that way.

The ink had a viscosity of 0.75 mPa·s. The particle size (maximum of number distribution) was 3 μm.

The material could be removed from the containers with a hair brush and applied well to the skin. Likewise the material could be applied to the skin with the fibre tip pen. The colour delivery was homogeneous and gave good coverage and the surface of the film formed was pleasantly soft. The film did not tighten on the skin and did not crack open even due to movements of the application area.

The dried ink films obtained in that way had a high coverage capability, they were wipe-resistant and water-resistant.

The material formed a sediment which had a relative sediment height of 0.6 in the storage vessels after a storage period of three months at ambient temperature. By simply stirring up the material the sediment was re-dispersed and after the then subsequent application presented properties of unchanged quality: a renewed smear of colour, compared to that from the original, unstored material, was evidently identical, no colour drift was to be observed and the colour intensity was also identical to the unstored material.

Example 4

Water-Based Ink IV

| Raw material | Amount in % wt |
|---|---|
| AQUA | ad 100 |
| IRON OXIDE RED | 7.50 |
| FERRIC FERROCYANIDE 77510 | 2.50 |
| PPG-20 Tocophereth-5 | 4.70 |
| BUTYLENE GLYCOL | 10.00 |
| POTASSIUM SORBATE | 0.50 |
| Phenoxyethanol | 1.00 |
| Coco-glucoside | 3.00 |
| Polyurethane-34 + AQUA (60% wt AQUA) | 10.00 |

The water was provided, the pigments were added and ground up with a rotor-stator dispersing tool (Ultra-Turrax) at a maximum rotary speed for 10 minutes. In a separate container butylene glycol and PPG-20 Tocophereth-5 are melted at 50° C. and that mixture was quickly added with agitation to the pigment dispersion. Then in each case with agitation first the surfactant, thereafter the preserving agents and lastly the polymer dispersion were added. The mixture was agitated for a further 15 minutes and introduced into fibre tip pens and into containers of a 4 ml filling capacity. A brown ink was obtained in that way.

The ink had a viscosity of 13 mPa·s. The particle size (maximum of number distribution) was 0.35 μm.

The material could be removed from the containers with a hair brush and applied well to the skin. Likewise the material could be applied to the skin with the fibre tip pen. The colour delivery was homogeneous and gave good coverage and the surface of the film formed was pleasantly soft. The film did not tighten on the skin and did not crack open even due to movements of the application area.

The dried ink films obtained in that way had a medium coverage capability, they were wipe-resistant and water-resistant.

The material formed a sediment which had a relative sediment height of 0.3 after a storage period of three months at ambient temperature. By simply stirring up the material the sediment was re-dispersed and after the then subsequent application presented properties of unchanged quality: a renewed smear of colour, compared to that from the original, unstored material, was evidently identical, no colour drift was to be observed and the colour intensity was also identical to the unstored material.

Comparative Example 1

Water-Based Ink

| Raw material | Amount in % wt |
| --- | --- |
| TITANIUM DIOXIDE 77891 | 5.0 |
| Ferric Ferrocyanide | 5.0 |
| PEG/PPG 10/70 | 4.9 |
| Propylene glycol | 12.1 |
| Vinylpyrrolidone/vinylacetate copolymer solution in AQUA (80% wt AQUA) | 10.2 |
| SORBITAN LAURATE + POLYGLYCERYL-10 LAURATE | 5.5 |
| Potassium sorbate | 0.5 |
| Phenoxyethanol | 1.0 |
| Water | ad 100 |

The water was provided, the pigments were added and ground up with a rotor-stator dispersing tool (Ultra-Turrax) at a maximum rotary speed for 10 minutes. In a separate container propylene glycol and PEG/PPG-10/70 Tocophereth-100 are melted at 50° C. and that mixture was quickly added with agitation to the pigment dispersion. Then in each case with agitation first the surfactant, thereafter the preserving agents and lastly the polymer pre-dissolved in water were added. The mixture was agitated for a further 15 minutes and introduced into fibre tip pens and into containers of a 4 ml filling capacity. A blue ink was obtained in that way.

The ink had a viscosity of 12 mPa·s. The particle size (maximum of number distribution) was 0.45 μm.

The material could be removed from the containers with a hair brush and applied well to the skin. In comparison with the other materials the colour delivery from the felt tip pen was relatively thin, indicating settlement of the pigments. The colour delivery had streaks therethrough and had little coverage capacity. The film did not tighten on the skin, but exhibited fine cracks upon movements of the application area.

The dried ink films obtained in that way were of low coverage capability, somewhat wipe-resistant but not water-resistant. The colour film ran off completely when rinsing over the application area.

The material formed a sediment which had a relative sediment height of 0.2 after a storage period of three months at ambient temperature. The sediment was not completely re-dispersed by thorough stirring of the material. A small bottom sediment remained. As a result upon a renewed smear of colour, compared to that from the original unstored material, the material was not identical but was of lesser colour intensity and coverage.

Comparative Example 2

Water-Based Ink

| Raw material | Amount in % wt |
| --- | --- |
| TITANIUM DIOXIDE 77891 | 5.0 |
| Ferric Ferrocyanide | 5.0 |
| PPG-70 Tocophereth-100 | 4.9 |
| Propylene glycol | 12.1 |
| Vinylpyrrolidone/vinylacetate copolymer solution in AQUA (80% wt AQUA) | 9.8 |
| SORBITAN LAURATE + POLYGLYCERYL-10 LAURATE | 5.5 |
| Potassium sorbate | 0.5 |
| Phenoxyethanol | 1.0 |
| Water | ad 100 |

The water was provided, the pigments were added and ground up with a rotor-stator dispersing tool (Ultra-Turrax) at a maximum rotary speed for 10 minutes. In a separate container propylene glycol and PPG-70 Tocophereth-100 are melted at 50° C. and that mixture was quickly added with agitation to the pigment dispersion. Then in each case with agitation first the surfactant, thereafter the preserving agents and lastly the polymer pre-dissolved in water were added. The mixture was agitated for a further 15 minutes and introduced into fibre tip pens and into containers of a 4 ml filling capacity. A blue ink was obtained in that way.

The ink had a viscosity of 17 mPa·s. The particle size (maximum of number distribution) was 0.13 μm.

The material could be removed from the containers with a hair brush and applied well to the skin. In comparison with Examples 1 to 3 the colour delivery from the felt tip pen was somewhat thinner, but not as thin as in Comparative Example 1, indicating settlement of the pigments. The colour delivery had scarcely any streaks therethrough and had good coverage capacity. The film did not tighten on the skin, but exhibited fine cracks upon movements of the application area.

The dried ink films obtained in that way were of good coverage capability, wipe-resistant but not water-resistant. The colour film ran off completely when rinsing over the application area.

The material formed a sediment which had a relative sediment height of 0.33 in the storage vessels after a storage period of three months at ambient temperature. The sediment was not completely re-dispersed by thorough stirring of the material. A small bottom sediment remained. As a result upon a renewed smear of colour, compared to that from the original unstored material, the material was not identical but was of lesser colour intensity and coverage.

The invention claimed is:

1. A water-based pigmented preparation for use in capillary storage systems comprising at least one pigment comprising pigment particles, at least one water-dispersible film-forming component and at least one polymer ether component, wherein the polymer ether component is of the following formula:

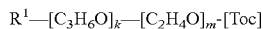

$$R^1-[C_3H_6O]_k-[C_2H_4O]_m-[Toc]$$

wherein $R^1$ is any alkyl residue, aromatic residue, acyl residue or H, k is a whole number >20, m is a whole number >5 and Toc is a tocopheryl residue, wherein the preparation contains the polymer ether component in an amount between 1 and 30% by weight of the preparation, wherein the polymer ether component has a ratio of propylene oxide units to ethylene oxide units of between 5:1 and 1:5.

2. A preparation according to claim 1 wherein in the polymer ether component k is a whole number ≥40.

3. A preparation according to claim 1 wherein in the polymer ether component k is a whole number ≥50.

4. A preparation according to claim 1 wherein in the polymer ether component k is a whole number ≥60.

5. A preparation according to claim 1 wherein in the polymer ether component m is a whole number ≥50.

6. A preparation according to claim 1, wherein in the polymer ether component m is a whole number ≥80.

7. A preparation according to claim 1, wherein in the polymer ether component m is a whole number ≥100.

8. A preparation according to claim 1 wherein the amount of polymer ether component is 1.5 to 10% by weight with respect to the total weight of the preparation.

9. A preparation according to claim 1 wherein the amount of polymer ether component is 2.0 to 5% by weight with respect to the total weight of the preparation.

10. A preparation according to claim 1 wherein the pigment is selected from the group consisting of a coloured pigment, a white pigment, a colour lacquer, a pearl sheen pigment and mixtures thereof.

11. A preparation according to claim 1 wherein the pigment is selected from the group consisting of iron oxides, titanium dioxide, zinc oxide, carbon black, carmine, ferric ferrocyanide, chromium hydroxide green, chromium oxide green, manganese violet, ultramarine blue and Yellow 5.

12. A preparation according to claim 1 wherein the amount of pigment is 1 to 20% by weight with respect to the total weight of the preparation.

13. A preparation according to claim 1 wherein the amount of pigment is 5 to 15% by weight with respect to the total weight of the preparation.

14. A preparation according to claim 1 wherein the amount of pigment is 7 to 12% by weight with respect to the total weight of the preparation.

15. A preparation according to claim 1 wherein the particle size of the pigments is less than 15 μm.

16. A preparation according to claim 1 wherein the particle size of the pigments is less than 10 μm.

17. A preparation according to claim 1 wherein the particle size of the pigments is less than 5 μm.

18. A preparation according to claim 1 wherein the water-dispersible film-forming component is selected from the group consisting of polyacrylate, polyurethane, polyester, polyvinyl acetate, derivatives, copolymers, block copolymers and mixtures thereof.

19. A preparation according to claim 1 wherein the amount of film-forming component is 1 to 30% by weight with respect to the total weight of the preparation.

20. A preparation according to claim 1 wherein the amount of film-forming component is 2 to 20% by weight with respect to the total weight of the preparation.

21. A preparation according to claim 1 wherein the amount of film-forming component is 4 to 10% by weight with respect to the total weight of the preparation.

22. A preparation according to claim 1 wherein the preparation contains at least one humectant, surfactant and preserving agent.

23. A preparation according to claim 1 wherein the preparation is one of a blusher, eyeliner, lip ink, lipliner, eye shadow, concealer, mascara, and eyebrow ink.

24. A pencil including a capillary storage system and a preparation according to claim 1.

25. A pencil according to claim 24 wherein the pencil is one of an eyeliner, a lipliner and an eyebrow pencil.

* * * * *